United States Patent [19]

Melinyshyn et al.

[11] Patent Number: 4,949,756
[45] Date of Patent: Aug. 21, 1990

[54] ONE-WAY VALVE

[75] Inventors: Lev Melinyshyn, Mt. Prospect;
Edward M. Goldberg, Glencoe, both of Ill.

[73] Assignee: Uresil Corporation, Skokie, Ill.

[21] Appl. No.: 237,849

[22] Filed: Aug. 31, 1988

[51] Int. Cl.⁵ .............................................. F16K 15/14
[52] U.S. Cl. ..................................... 137/846; 604/247
[58] Field of Search ............... 137/843, 844, 846, 850; 604/247

[56] References Cited
U.S. PATENT DOCUMENTS

| 3,463,159 | 8/1969 | Helmlich | 137/846 X |
| 3,491,791 | 1/1970 | Polk | 137/844 |
| 4,416,308 | 11/1983 | Bower | 137/846 |
| 4,708,167 | 11/1987 | Koyanagi | 137/846 X |

Primary Examiner—Robert G. Nilson
Attorney, Agent, or Firm—Hosier & Sufrin, Ltd.

[57] ABSTRACT

A one-way valve comprising flat resilient members in face-to-face relationship which are bonded upon two generally parallel tracks defining a passageway therebetween, where the tracks have a tortuous profile along their inner edges, and optionally, where the passageway is creased and/or wetted.

11 Claims, 2 Drawing Sheets

FIG. 8
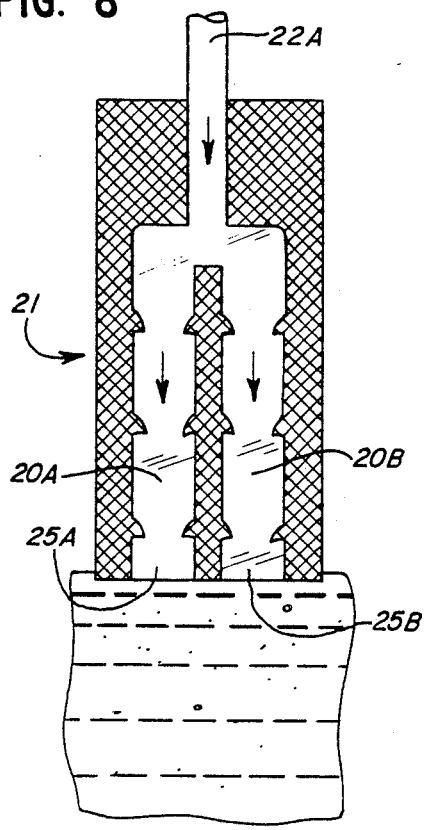
FIG. 9
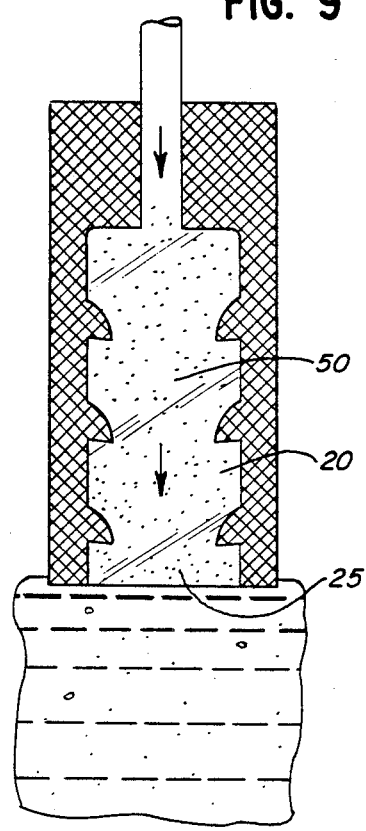
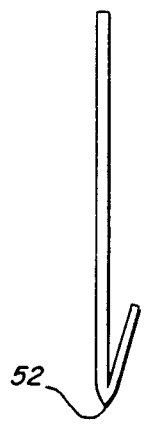
FIG. 10
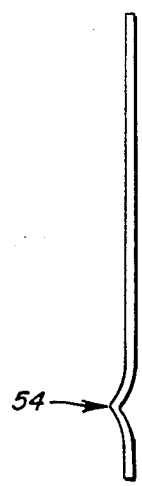
FIG. 11

ONE-WAY VALVE

BACKGROUND OF THE INVENTION

This invention relates generally to one-way valves. More particularly, this invention relates to improved one-way valves constructed from flat resilient members bonded in face-to-face relationship.

The term "one-way valve" is intended to mean a device which allows the passage of substances through it in one direction only. Such valves are used in a host of applications, including medical applications, where fluids must be withdrawn from body cavities without reflux to the cavities.

It is most desirable to be able to achieve low "crack" resistance in one-way valves, so that the valves will open in the desired direction of flow on the application of minimal pressure. Similarly, it is most desirable to maximize reflux sensitivity of such valves, so that they will close quickly to prevent back-flow through the valve. It is likewise important that the valves continue to operate when particulate matter becomes lodged in the valves.

In many applications requiring one-way valves, it is important that the valves be compact and flexible, so that they do not occupy excessive space in the devices in which they are employed.

Finally, it is often important that the valves have a long shelf life, so that they will be reliable whenever the devices in which they employed are put to use. In addition, for medical applications, the valves must be constructed from materials approved for use in the treatment of human subjects, and they often must be able to stand up to drastic pressure changes and to a lesser degree to temperature and humidity changes, all as part of sterilization procedures.

SUMMARY OF THE INVENTION

It is therefore one important object of the present invention to provide a highly sensitive one-way valve which has low crack resistance and high reflux sensitivity.

It is a further object of the present invention to provide a one-way valve which continues to function when particulate matter becomes lodged in its passageway.

It is another object of the present invention to provide a one-way valve which occupies minimum space in the devices in which it is employed.

Yet another object of the present invention is to provide a one-way valve which is particularly well suited to applications in medical apparatus, by virtue of its construction from materials approved for use in medical applications.

It is yet a further object of the present invention to provide a one-way valve which is structurally simple, readily fabricated and highly reliable over extended periods of time.

Finally, it is an object of the present invention to provide a highly sensitive one-way valve with high reflux sensitivity which will retain its reflux sensitivity when the valve is subjected to pressure, temperature and humidity changes, as in, for example sterilization procedures.

These and other objects of the present invention will be apparent from the discussion below.

The present invention is therefore directed to a one-way valve comprising two flat resilient members in face-to-face relationship with each other. The resilient members are bonded along two generally parallel tracks which define a passageway therebetween. The tracks have a tortuous profile along their inner edges. Finally, inlet and outlet ports are provided at the opposing ends of the passageway.

BRIEF DESCRIPTION OF THE DRAWINGS

The features of this invention which are believed to be novel are set forth with particularity in the appended claims. The invention, together with its objects and advantages thereof, may be best understood by reference to the following description taken in conjunction with the accompanying drawings, in which like reference numerals identify like elements in the several figures and in which:

FIG. 8 is a one-way valve constructed in accordance with the present invention which includes two passageways;

FIG. 9 is a plan view fo the one-way valve of FIG. 1 in which silicone oil has been introduced between the opposing faces of the resilient members;

FIG. 10 is a side view of the valve of FIG. 9, in which the valve has been creased across the passageway; and FIG. 11 is a side view of the valve of FIG. 10 after the folded valve is released.

DESCRIPTION OF THE PREFERRED EMBODIMENTS

Figure 1:
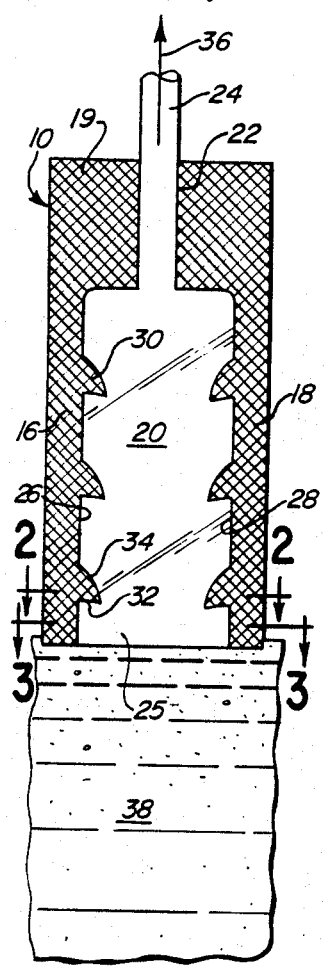
FIG. 1 is a plan view of a one-way valve constructed in accordance with the present invention.
Figure 2:
FIG. 2 is a cross-sectional view of the valve of FIG. 1, taken along lines 2—2 thereof.
Figure 3:
FIG. 3 is a cross-sectional view of the valve of FIG. 1, taken along lines 3—3 thereof.

Turning now to FIGS. 1–3, a one-way valve 10 is illustrated, including flat resilient members 12 and 14 in face-to-face relationship with each other. Flat resilient members 12 and 14 are bonded along generally parallel tracks 16 and 18 which define a passageway 20 therebetween.

Tracks 16 and 18 come together near the top of the valve 19 to define an inlet port 22 which is narrower than passageway 20. Inlet port 22 is sealingly attached to a rigid conduit 24. Valve 10 is also provided with an outlet port 25 at the opposite end of passageway 20.

Tracks 16 and 18 each have a tortuous profile along their respective inner edges 26 and 28. In the embodiment illustrated, the tortuous profile comprises a series of sawteeth 30 projecting from each of the track inner edges into passageway 20. Each sawtooth has a leading edge 32 and a trailing edge 34. The sawteeth are positioned with their leading edges oriented toward the outlet port and their trailing edges oriented towards the inlet port. In an alternate. somewhat less desirable embodiment a single sawtooth may be used at each of the track inner edges.

The tortuous profile may take various different forms which create twists, turns, curves and windings along the outer edges of passageway 20 to prevent reflux flow along the outer edges of the valve passageway, as explained below.

When a suction force is applied to conduit 24, as indicated by the arrow 36, the valve takes on the respective cross-sectional profiles illustrated in FIGS. 2 and 3. Thus, any fluid 38, which is drawn up along the initial generally straight edges of passageway 20 at outlet port 25 (FIG. 3) will not pass throught the valve, as explained below in connection with the discussion regarding FIGS. 6 and 7.

Resilient materials including for example, polyethylene, mylar, nylon and polyvinyl chloride. All of these materials are approved for use in the treatment of human subjects. The resilient members should be from about 1 to about 10 mils in thickness, although it is preferred that the resilient members be from about 3 to about 5 mils thick. In a particularly preferred embodiment, the resilient members will be about 3 mils in thickness.

The resilient members may be bonded to each other and to rigid conduit 24 by an conventionally available means which would not unduly restrict the operation of the valve. It is preferred that the resilient layers be bonded by a heat sealing technique such as thermal impulse heating or hot bar heating. Among presently available bonding techniques, thermal impulse heating has been found to be particularly desirable. The temperatures, pressures and other parameters used in bonding the resilient members will depend upon the material of the resilient members, their thickness, the length and width of the valve, and the desired valve crack resistance and reflux sensitivity.

In one preferred embodiment in which heat-sealing bonding method is used, the resilient members are laminates comprising a heat-sealable layer and a thermally-resistant layer. In this embodiment, the thermally-resistant layer primarily governs the physical properties of the valve while the heat-sealable layer bonds the resilient members. These laminated resilient members are disposed in the valve with their heat-sealable layers in face-to-face relationship. Thus, the heat-sealable layers will melt and adhere during the bonding process at a bonding temperature which will not significantly alter the resilience, integrity, and other necessary and desirable characteristics of the thermally-resistant layer.

The laminated resilient layers may be made by any known means, including conventional lamination and coextrusion techniques. Also, where a laminated material is used, the heat-sealable layer should be from about 2.5 to about 3.5 mils in thickness and the thermally-resistant layer should be from about 0.50 to about 0.75 mils in thickness. In a particularly preferred embodiment, the heat-sealable layer should be about 3.0 mils in thickness and the thermally-resistant layer should be about 0.75 mils in thickness.

The heat-sealable layer of the laminated resilient members may be chosen from the group consisting of low density polyethylene and ethyl vinyl actate. The thermally-resistant layer may be chosen from the group consisting of nylon, mylar and linear low density polyethylene. A particularly preferred laminated material, comprising low density polyethylene and nylon, can be made by laminating low density polyethylene to Capran film available from Allied Engineered Plastics of Mooristown, N. J. This laminated material takes on certain desirable characteristics of the nylon including outstanding resistance to puncture, abrasion and flex cracking, as well as high burst and impact strength and high tensile and tear strength.

Although the valve illustrated in FIG. 1 shows a single pair of tracks 16 and 18 and a single passageway 20, as illustrated in FIG. 8, one-way valve 21 in accordance with the present invention may have two or more pairs of sealing tracks defining a plurality of passageways 20A and 20B with the passageways having a single common inlet 22A and a plurality of independent outlet ports 25A and 25B. In addition, one-way valves in accordance with the teaching of the present invention may be made in various lengths and widths to tailor the valve properties to the desired applications.

The valve illustrated in FIG. 1 can be used in medical applications, for example, to drain fluid and gases from the chest, where it is essential that the liquids and gases be permitted to escape without reflux. In this application, it is important that the valve prevent blood clots and other solids expelled from the chest cavity from causing valve failure.

Figure 4:
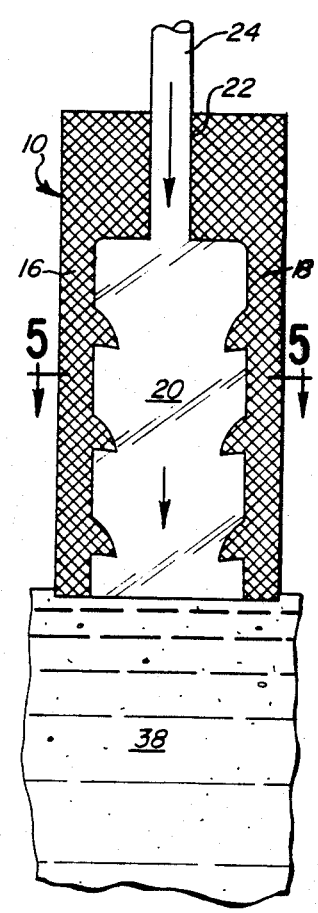
FIG. 4 is a plan view of the valve of FIG. 1 illustrating flow of fluid therethrough.

Thus, rigid conduit 24 would be connected to a drain placed in the chest cavity (not shown). As illustrated in FIG. 4, gases and fluids expelled from the chest cavity flow through conduit 24, inlet port 22 and passageway 20 into a receptacle (not shown) containing liquid 38. When a suction force is applied to the conduit, the valve closes, as illustrated in FIGS. 1–3, to prevent liquids and gases from being drawn back up through the valve and into the chest cavity. Due to the design of the valve, blood clots and other solids which may be introduced into passageway 20 during the draining procedure are held in place and will not interfere with the operation of the valve. The opposing faces of resilient members 16 and 18 simply seal above and below such solids without hindering valve function.

Figure 6:
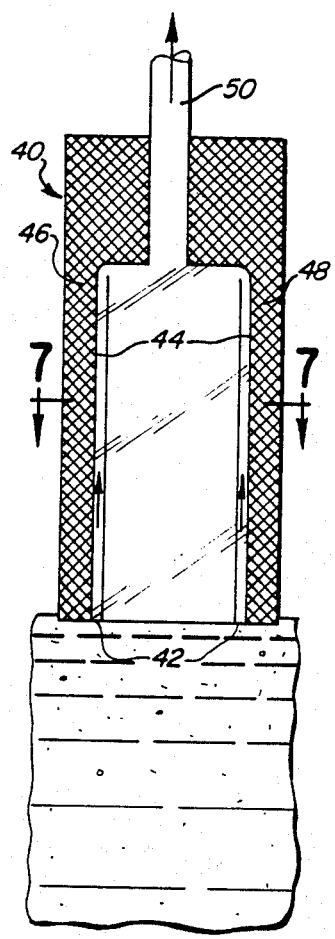
FIG. 6 is a plan view of a one-way valve lacking the tortuous passageway profile of the present invention.
Figure 7:
FIG. 7 is a cross-sectional view of the valve of FIG. 6, taken along lines 7—7 thereof.
Figure 5:
FIG. 5 is a cross-sectional view of the valve of FIG. 4, taken along lines 5—5 thereof.

While the invention is not intended to be limited by any particular theory of the operation of valve 10, in the absence of a tortuous profile, as in the valve 40 illustrated in FIGS. 6 and 7, fluid leakage results under high suction forces. Apparently, such leakage occurs due to the formation of small channels 42 along the inner edges 44 of tracks 46 and 48 which permit fluids (liquids or gases) to travel up the valve when suction is applied to conduit 50.

The tortuous profile in valve 10 (FIG. 1) interrupts the channels which otherwise form along the outer edges of the valve passageway, redirecting the flow toward the center of the passageway where it is effectively blocked. The tortuous profile is also believed to maintain the opposing faces of resilient members 12 and 14 in enhanced intimate contact to improve the reflux sensitivity of the valve.

In another preferred embodiment of the invention, illustrated in FIGS. 9–11, a wetting agent 50 is introduced into passageway 20 to "wet" the inner opposing faces of the resilient members of the valve. Wetting agents have been found to improve the reflux sensitivity of the valve. In addition, although the operation of the valve may be impaired when it is subjected to pressure, temperature and humidity changes, as in, for example, a sterilization procedure, addition of a high boiling liquid as the wetting agent will maintain or restore the valve function.

The principal criteria in choosing the wetting agent are that it will not degrade or damage the valve material, that it will not boil off, that it will not deposit particulate matter in the valve, and that it will not cause the opposing faces fo the valve to permanently adhere to each other. Oils meeting the above criteria are the preferred agents. A particularly preferred wetting agent is silicone oil, because of its high boiling point and wetting properties and also because it is a material approved for use in medical devices.

In yet another preferred embodiment, a crease 54 (FIG. 11) is made across passageway 20. The crease may be made by sharply folding the valve at 52 (FIG. 10), preferably near outlet port 25, and then releasing the valve. The valve will return almost to its initial planar leaving the side profile of the modified valve slightly bent as illustrated in FIG. 11.

As in the case of the addition of a wetting agent, the crease will improve the reflux sensitivity of the valve and will restore valve function lost due to pressure, temperature and humidity changes encountered in sterilization or other procedures. The crease may be placed in the valve either before exposure to such treatments or after, although application of the crease before heating is preferred.

Finally, in a most preferred embodiment of the invention, the combination of the wetting agent and the crease have been found to significantly improve the reflux sensitivity of the valve under all conditions, including particularly when the valve is subjected to pressure, temperature and humidity changes, which would otherwise impair valve function.

While particular embodiments of the invention have been shown and described, it will be obvious to those skilled in the art that various changes and modifications may be made therein without departing from the spirit and scope of the invention and, therefore, it is intended in the appended claims to cover all such changes and modifications which fall within the true spirit and scope of the invention.

What we claim is:

1. A one-way valve comprising:
   two flat resilient members in face-to-face relationship with each other, said resilient members being bonded along two generally parallel tracks defining a passageway therebetween, said tracks having a tortuous profile along their inner edges;
   a wetting agent wetting said opposing faces of said resilient members; and
   an inlet port at one end of said passageway and an outlet port at the opposite end of the passageway.

2. The one-way valve of claim 1 wherein the wetting agent is an oil.

3. The one-way valve of claim 2 wherein the wetting agent is silicone oil.

4. A one-way valve comprising:
   two flat resilient members in face-to-face relationship with each other, said resilient members being bonded along two generally parallel tracks defining a passageway therebetween said passageway containing a wetting agent and said tracks further having a tortuous profile along their inner edges;
   a crease across said passageway; and
   an inlet port at one end of said passageway and an outlet port at the opposite end of the passageway.

5. The one-way valve of claim 14 wherein said wetting agent is silicone oil.

6. The one-way valve of claim 4 wherein said resilient members are made from a material chosen from the group consisting of polyethylene, mylar, nylon and polyvinyl chloride.

7. The one-way valve of claim 6 wherein each of said resilient layers is a laminate of low density polyethylene and nylon.

8. The one-way valve of claim 4 wherein each of said resilient members has a heat-sealable layer and a thermally-resistant layer, and resilient members being disposed with their heat-sealable layers in face-to-face relationship.

9. The one-way valve of claim 8 wherein said heat-sealable layer is chosen from the group consisting of low density polyethylene and ethyl vinyl acetate and the thermally-resistant layer is chosen from the group consisting of nylon, mylar, linear low density polyethylene.

10. A one-way valve comprising:
    two flat resilient members in face-to-face relationship with each other, said resilient members being bonded along two generally parallel tracks defining a passageway therebetween, said tracks having a tortuous profile along their inner edges;
    a crease across said passageway; and
    an inlet port at one end of said passageway and an outlet port at the opposite end of the passageway.

11. The one-way valve of claim 10 wherein said crease is located near said outlet port.

* * * * *